US006403096B1

(12) United States Patent
Epstein et al.

(10) Patent No.: US 6,403,096 B1
(45) Date of Patent: Jun. 11, 2002

(54) VASOPERMEABILITY ENHANCING PEPTIDE OF HUMAN INTERLEUKIN-2 AND IMMUNOCONJUGATES THEREOF

(75) Inventors: Alan L. Epstein, La Canada; Leslie A. Khawli, Arcadia, both of CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 09/443,061

(22) Filed: Nov. 18, 1999

Related U.S. Application Data

(62) Division of application No. 08/806,121, filed on Dec. 23, 1996, now Pat. No. 6,008,319.

(51) Int. Cl.$^7$ .......................... A61K 38/20; A61K 51/02

(52) U.S. Cl. .................. 424/195.11; 530/324; 530/351; 530/402; 514/2; 514/8; 514/12; 424/192.1; 424/85.2

(58) Field of Search ................................ 530/324, 402, 530/388.1, 387.3, 388.15, 387.1, 351; 435/320.1, 325; 514/2, 4, 8

(56) References Cited

U.S. PATENT DOCUMENTS

| | | | |
|---|---|---|---|
| 4,518,584 A | 5/1985 | Mark et al. ..................... 424/85 |
| 4,738,927 A | 4/1988 | Taniguchi et al. ........... 435/243 |
| 4,780,313 A | 10/1988 | Koichiro et al. ............... 424/88 |
| 4,832,940 A | 5/1989 | Ege ............................. 424/1.1 |
| 4,894,227 A | 1/1990 | Stevens et al. ............. 424/85.2 |
| RE33,653 E | 7/1991 | Mark et al. |

FOREIGN PATENT DOCUMENTS

EP   0 163 249 B1   7/1991

OTHER PUBLICATIONS

Ahmad, A., et al., "Recombinant targeted proteins for biotherapy", *Mol. Biother.*, 2:67–73 (1990).
Antoni, G., et al., "A Short Syntetic Peptide Fragment of Human Interleukin 1 With Immunostimulatory But Not Inglammatory Activity", *J. Immunol.*, 137:3201–3204 (1986).
Bazan, J. F., "Unraveling the Structure of IL–2", *Science*, 257:410–412 (1992).
Cohen, F. E., et al., "Structure–Activity Studies of Interleukin-2", *Science*, 234:349–352 (1986).
Epstein, A. L., et al., Two New Monoclonal Antibodies, Lym–1 and Lym–2, Reactive with Human B–Lymphocytes ands Derived Tumors, with Immunodiagnostic and Immunotherapeutic Potential, *Cancer Res.*, 47: 830–840 (1987).
Epstein, A. L., et al., "A Novel Method for the Detection of Necrotic Lesions in Human Cancers", *Cancer Res.*, 48:5842–5848 (1988).

Epstein, A. L., et al., "Identification of a Monoclonal Antibody, TV–1, Directed against the Basement Membrane of Tumor Vessels, and Its Use to Enhance the Delivery of Macromolecules to Tumors after Conjugation with Interleukin 2", *Cancer Res.*, 55:2673–2680 (1995).
Epstein, A. L., "Tumor Necrosis Imaging and Treatment of Solid Tumors," pp. 259–288 in *Handbook of Targeted Delivery of Imaging Agents*, V. P. Torchilin, Ed.,CRC Press (1995).
Epstein, A. L., "New Approaches to Improved Antibody Targeting," pp. 516–533 in *Nuclear Medicine, vol. 1*, R. E. Henkin, Ed., Mosby–Year Book (1996).
Gillies, S. D., et al., "Expression of Genetically Engineered Immunoconjugates of Lymphotoxin and a Chimeric Anti–Ganglioside GD2 Antibody", *Hybridoma*, 10:347–355 (1991).
Gillies, S. D., et al., "Antibody–targeted interleukin 2 stimulates T–cell killing of autologous tumor cells", *Proc. Natl. Acad. Sci., USA*, 89:1428–1432 (1992).
Hu, P., et al., "A human–mouse chimeric Lym–1 monoclonal antibody with specificity for human lymphomas expressed in a baculovirus system", *Hum. Antibod. Hybridomas* 6 (1):57–67 (1995).
Imler, J. –L., et al., "Identification of three adjacent amino acids of interleukin–2 receptor β chain which control the affinity and the specificity of the interaction with interleukin–2", *The EMBO Journal*, 11:2047–2053 (1992).
Kaplan, D., et al., "Self–association of interleukin 2 bound to its receptor", *The FASEB Journal*, 9:1096–1102 (1995).
Khawli, L. A., et al., "Effect of Seven New Vasoactive Immunoconjugates on the Enhancement of Monoclonal Antibody Uptake in Tumors", *Cancer*, 73:824–831 (1994).
Kiyokawa, T., et al., "Protein engineering of diphtheria–toxin, related interleukin–2 fusion toxins to increase cytotoxin protency for high–affinity IL–2–receptor–bearing target cells", *Protein Engineering*, 4:463–468 (1991).
Landgraf, B. E., et al., "Recombinant Interleukin–2 Analogs", *J. Biol. Chem.*, 267:18511–18519 (1992).
Landolfi, N. F., "A Chimeric IL–2/Ig Molecule Possesses The Functional Activity Of Both Proteins", *J. Immunol.*, 146:915–919 (1991).

(List continued on next page.)

Primary Examiner—Lorraine Spector
Assistant Examiner—Sanada C Prasad
(74) Attorney, Agent, or Firm—Fulbright & Jaworski

(57) ABSTRACT

A novel permeability enhancing peptide (PEP) is a fragment of interleukin-2. When joined to a delivery vehicle that can target a tumor site, the PEP can increase the subsequent uptake of antineoplastic or tumor imaging agents. The PEP can be chemically joined to a monoclonal antibody to form an immunoconjugate. Alternatively, an expression vector is genetically engineered to express a fusion protein. The fusion protein has an antigen-binding portion joined to the PEP. The PEP is most effective when it takes the form of a dimer, linked by a disulfide bridge. The PEP is substantially free of cytokine activity and produces minimal toxic side effects on normal tissues.

4 Claims, 5 Drawing Sheets-

OTHER PUBLICATIONS

LeBerthon, B., et al., "Enhanced Tumor Uptake of Macromolecules Induced by a Novel Vasoactive Interleukin 2 Immunoconjugate", *Cancer Res.*, *51*:2694–2698 (1991).

LeMaistre, C. F., et al., "Phase I Trial of an Interleukin–2 (IL–2) Fusion Toxin ($DAB_{486}$ IL–2) in Hematologic Malignancies Expressing the IL–2 Receptor", *Blood*, *79*:2547–2554 (1992).

Lotze, M. T., "Interleukin–2", in *Human Cytokines*, Ed. by Aggarwal and Gutterman, pp. 81–96, (1992).

Marincola, F. M., "Interleukin–2", in *Biologic Therapy of Cancer Updates*, *4*(*3*):1–16 (1994).

McKay, D. B., "Unraveling the Structure of IL–2: Response", *Science* 257:412–413 (1992).

Naramura, M., et al., "Mechanisms of cellular cytotoxiity mediated by a recombinant antibody–IL2 fusion protein against human melanoma cells", *Immunol. Lett.*, *39*:91–99 (1994).

Savage, P., et al., "A recombinant single chain antibody interlelukin–2 fusion protein", *Br. J. Cancer*, *67*:304–310 (1993).

Taniguchi, T., et al., "Structure and expression of a cloned cDNA for human interleukin–2", *Nature*, *302*:305–310 (1983).

Vuist, W. M. J., et al., "Two Distinct Mechanisms of Antitumor Activity Mediated by the Combination of Interleukin 2 and Monoclonal Antibodies", *Cancer Res.*, *50*:5767–5772 (1990).

Wang, A., et al., "Site–Specific Mutagenesis of the Human Interleukin–2 Gene: Structure–Function Analysis of the Cysteine Residues", *Science*, *224*:1431–1433 (1984).

FIG. 1A

22
CAG ATG ATC CTG AAC AAC GGT ATC AAC AAC TAC AAG AAC CCG AAA CTG ACT CGT ATG CTG    40
Gln Met Ile Leu Asn Asn Gly Ile Asn Asn Tyr Lys Asn Pro Lys Leu Thr Arg Met Leu

41
ACC TTC AAG TTC TAC ATG CCG AAG AAA GCT ACC GAA CTG AAA CAC CTG CAA TGC    58
Thr Phe Lys Phe Tyr Met Pro Lys Lys Ala Thr Glu Leu Lys His Leu Gln Cys

FIG. 2A
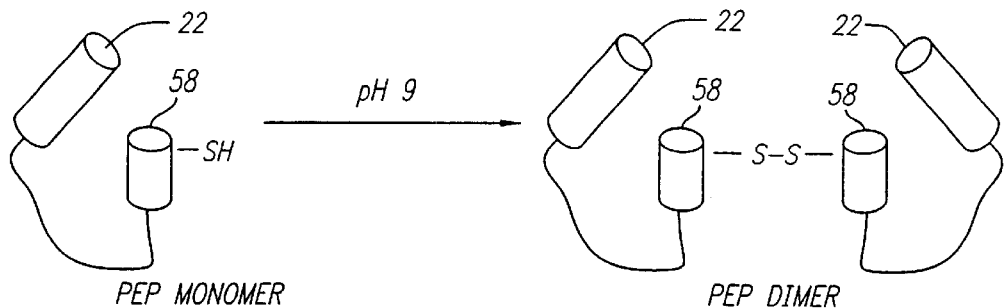
FIG. 2B
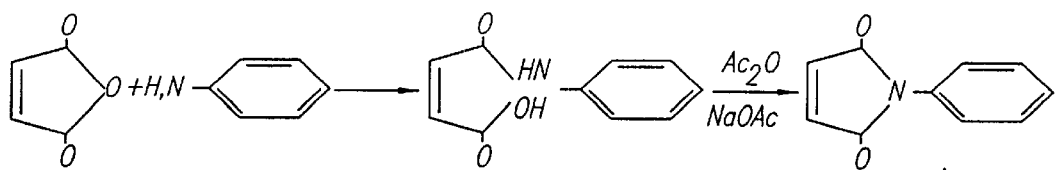
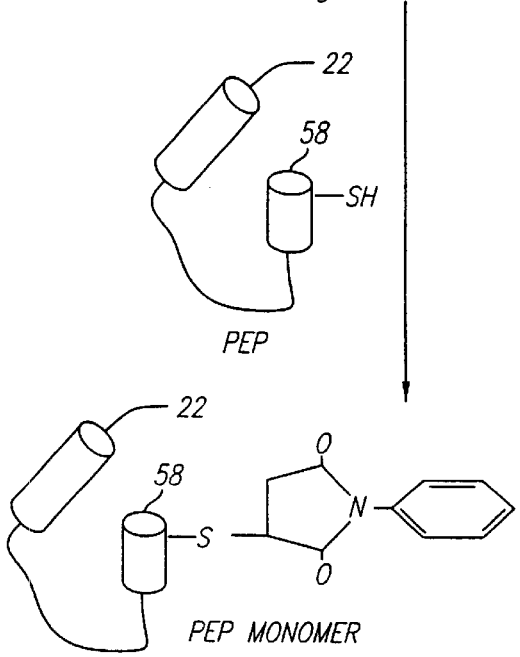

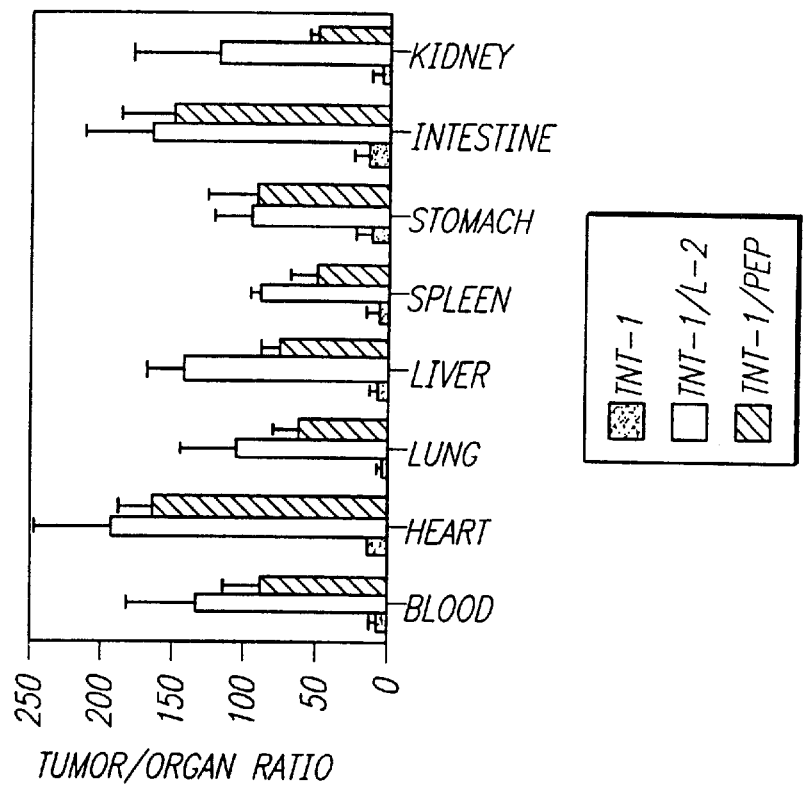
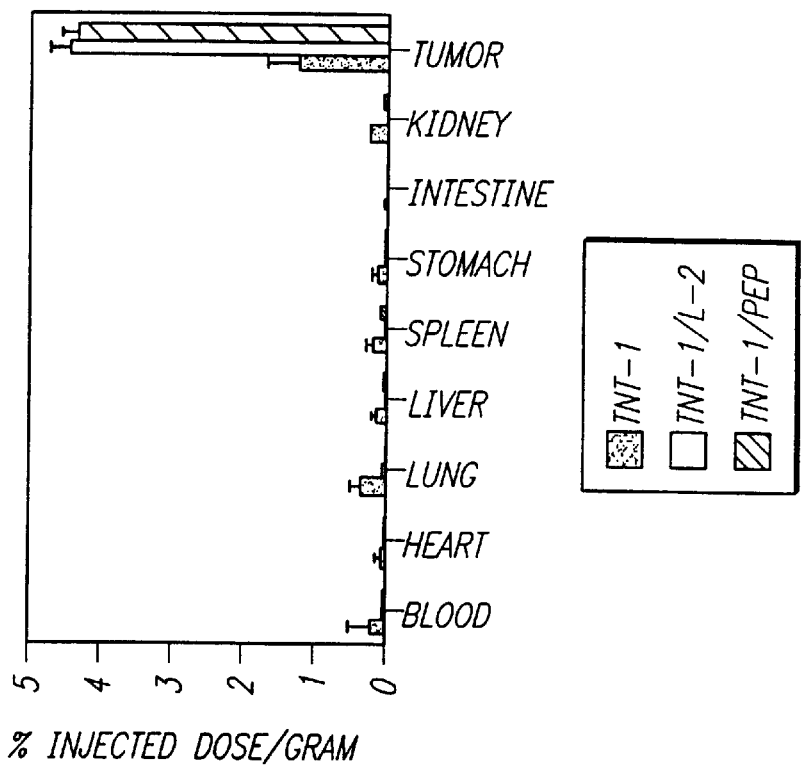

VASOPERMEABILITY ENHANCING PEPTIDE OF HUMAN INTERLEUKIN-2 AND IMMUNOCONJUGATES THEREOF

This is a divisional of U.S. patent application Ser. No. 08/806,121, filed Dec. 23, 1996 now U.S. Pat. No. 6,008,319.

BACKGROUND OF THE INVENTION

The ability of monoclonal antibodies (MAbs) to target and accumulate in tumors has been amply demonstrated in both animal models and man. Although the specificity of this targeting varies with different MAbs, the amount of antibody that binds tumor, relative to the amount that binds normal tissue has been high enough to permit clear tumor images using appropriate radioactive labels.

For therapy, however, the quantity of antibody that accumulates at the tumor site determines the payload of therapeutic radionuclide, toxin, or drug delivered to the tumor. Early studies measuring the percent injected dose found in tumors in patients after injection with radiolabeled MAbs have shown extremely low values on the order of 0.01–0.1%. (See, e.g., Goldenberg, D. M., Arch. Pathol. Lab. Med. 112: 580–587 (1988); Epenetos et al., Cancer Res. 46: 3183–3191 (1986)). Considering the relative resistance of most malignant solid tumors to drugs and radiotherapy, it is imperative that the accumulation of MAbs at the tumor site be substantially improved to obtain an adequate therapeutic index required for maximum tumor destruction and sustained therapy.

In order to improve the effectiveness of monoclonal antibody (MAb) therapy, a number of investigators have produced immunoconjugates composed of MAbs and biological response modifiers, such as cobra venom factor (Vogel, C. and Muller-Eberhard, H., Proc. Natl. Acad. Sci., USA, 78(12): 7707–7711 (1981), Vogel, C. et al., "Hematology and Blood Transfusion," in Modern Trends in Human Leukemia VI, 29: 514–517 (1985), Rolf Neth, Ed.), formyl-methionyl-leucyl-phenylalanine (Obrist, R. Sandberg, A., Cellular Immunology 81: 169–174 (1983); Obrist, et al., Bent 53: 251 (1986)), and interferon-γ (Flannery, G. et al., Eur. J. Cancer Clin. Oncol., 20(6): 791–798 (1984)). These studies demonstrated that immunoconjugates could direct specific responses, like tumoricidal effects or chemotaxis, specifically to the tumor site without demonstrable toxicity in normal organs and tissues. However, this approach to enhancing the effectiveness of monoclonal antibody therapy did not solve the problem that only extremely low levels of monoclonal antibody accumulate at the tumor site.

Another approach to this problem is to alter the physiology of tumor vessels to enhance the tumor uptake of macromolecules. This approach used MAbs as carriers for the delivery of vasoactive peptides and compounds to the tumor. Seven different vasoactive compounds, namely tumor necrosis factor α, interleukin-1β, interleukin-2 (IL-2), physalaemin, histamine, bradykinin, or leukotriene, were chemically linked to a monoclonal antibody that targets degenerating cells in necrotic regions of tumors. While all of seven immunoconjugates showed specific enhancement of monoclonal antibody uptake in tumors, the IL-2/MAb conjugate gave the highest percent injected dose per gram of tumor. (Khawli, et al., Cancer 73: 824–831 (1994))

Interleukin-2 is a promising candidate for efforts to improve the therapeutic index of MAb therapy. It is a 15,000 Dalton protein produced by helper T lymphocytes. As a potent biological modulator of the immune system of animals and man, it occupies a central role in the augmentation of cell-mediated immune responses. Its major functions include the proliferation of T lymphocytes (Morgan, D. A, et al., Science 193: 1007–1008, (1976)) and the generation of non-specific tumor killing by activated macrophages, lymphokine-activated killer cells (LAK cells) (Grimm, E. A., et al., J. Exp. Med. 155: 1823–1841(1982)), and tumor infiltrating lymphocytes (TIL cells)(Rosenberg, S. A., et al., Science 233: 1318–1321(1986)). In addition to its cytokine activity, IL-2 has been shown to produce vascular permeability when administered systemically by causing the efflux of intravascular fluids to the extravascular spaces (capillary leak syndrome)(Rosenstein, M., et al., Immunology 137: 1735–1742 (1986); Ohkubo, C., et al., Cancer Res. 51: 1561–1563 (1991); Edwards, M. J., et al., Cancer Res. 52: 3425–3431(1992); Damle, N. K., et al., J. Immunol. 142: 2660–2669 (1989)).

Human IL-2 is a globular protein consisting of 133 amino acids and is similar in structure to Interleukin-4 and Granulocyte/Macrophage-Colony Stimulating Factor (GM-CSF)(Bazan, J. F., Science 257: 410–412 (1992)). Structural studies of IL-2 show that it is composed of four major amphipathic alpha helices arranged in an antiparallel fashion, with the hydrophobic faces making a very stable hydrophobic core (Bazan, J. F.,(1992); McKay, D. B., Science 257: 412–413 (1992)). In addition, one disulfide bond is important to stability of the tertiary structure and is essential for the biologic activity of IL-2 (Landgraf, B. E., Proteins 9: 207 (1991)). Loss of this disulfide bond, as well as even minor changes in the primary or secondary structure abrogate IL-2 cytokine activity as shown by site-directed mutagenesis studies (Cohen et al., Science 234: 349–352 (1986)). Previous studies have shown that the intact, native IL-2 structure is a prerequisite for biologic activity because of the unique structure of the IL-2 receptor, which may be low affinity (α chain), intermediate affinity (β and γ chains), or high affinity (α, β, and γ chains)(Smith, K. A., Blood 81: 1414–1423(1993)).

When IL-2 is used alone as a therapeutic agent or in combination with other agents, such as interferon-α, LAK, TILs, or monoclonal antibodies, 20–50% partial and complete responses are obtained in certain human neoplasms, including lymphoma, renal cell cancer, and melanoma (Lotze, M. T., "Interleukin-2," in Human Cytokines, Ed. by Aggarwal and Gutterman, pp. 81–96 (1992); Marincola, F. M., Biologic Therapy of Cancer Updates 4(3): 1–16 (1994); Thompson, J. A., et al., Hematologic Growth Factors 2(5): 351–355 (1994)). IL-2's activity against cancer has been ascribed to its ability to mediate enhanced host immune resistance, primarily through T-cell expansion and directing the traffic into tissues of such activated T-cells. However, the administration of IL-2 causes several systemic effects tied to the capillary leak syndrome, including edema formation, hypotension, and renal dysfunction. These side effects limit the administration of higher dosages of IL-2 and can lead to discontinuation of the therapy.

One approach to reducing the toxic effects of systemic IL-2 administration would be to target IL-2 to a tumor site using an antibody delivery system. Consequently, IL-2 has been successfully incorporated into a number of immunoconjugates and fusion proteins. A number of investigators have demonstrated that IL-2 cytokine activity can be preserved in such constructs. For example, Gillies et al. (Proc. Natl. Acad. Sci., USA 89, 1428–1432 (1992)) assembled a genetically engineered fusion protein consisting of a chimeric anti-ganglioside GD2 antibody and IL-2, which could enhance the killing of GD2-expressing melanoma target cells by a TIL cell line. Similarly, Savage et al. (*Br. J. Cancer* 67: 304–310 (1993)) constructed a single chain antibody IL-2 fusion protein that retained the ability to bind antigen as well as low affinity IL-2 receptors and to stimulate the proliferation of human peripheral blood lymphocytes. Moreover, Naramura et al. (*Immunol. Lett.* 39: 91–99 (1994)) demonstrated that a genetically engineered fusion protein, comprised of IL-2 and a mouse/human chimeric monoclonal antibody directed against human epidermal growth factor, activated immune effector cells in vitro and enhanced cellular cytotoxicity against human melanoma cells.

In contrast to work capitalizing on IL-2's cytokine activities, another approach focussed on harnessing its toxicity. For example, IL-2 has been covalently linked to a tumor-specific monoclonal antibody (MAb/IL-2) to induce localized vasopermeability at the tumor site (Khawli, et al.,(1994); LeBerthon et al., *Cancer Res.* 51: 2694–2698 (1991)). The generation of leaky tumor endothelium by pretreatment with MAb/IL-2 produced a 3–4 fold increase in monoclonal antibody uptake, which was not observed in normal tissues. Unlike the previous studies cited above (Gillies et al., Savage et al., and Naramura et al.), the chemistry used to link the IL-2 to monoclonal antibodies destroyed the cytokine activity of IL-2 without affecting its vasopermeability effects.

Taken together, these studies emphasize the finding that the vasopermeability activity of IL-2 appears to be a stable property of the molecule compared to the cytokine activity, which appears to be more sensitive to perturbations in the tertiary structure of IL-2. Consequently, it would be advantageous to develop a synthetic IL-2 peptide that retains the biologic activity of vasopermeability, but need not retain the cytokine activity of the molecule. Such a peptide may be used to generate potent vasoactive immunoconjugates, having reduced toxicity for normal tissues, that can be used to enhance the delivery of therapeutic and diagnostic agents in tumors and other tissues.

SUMMARY OF THE INVENTION

The present invention is directed to permeability enhancing peptides that satisfy the need for potent vasoactive agents, which improve the uptake of therapeutic and diagnostic agents at a tumor site. A vasoactive peptide having features of the present invention comprises a fragment of interleukin-2 that is substantially free of cytokine activity. The vasoactive peptide is capable of enhancing vascular permeability when joined to a carrier macromolecule, whereas the peptide alone is substantially less potent in vivo.

A particularly advantageous carrier macromolecule functions as a delivery vehicle, which can localize at the site of neoplastic tissue. The vasoactive peptide and delivery vehicle can be joined by a chemical reaction to form a conjugate. Alternatively, an expression vector can be genetically engineered to produce a fusion protein, which expresses a delivery vehicle joined to a permeability enhancing peptide (PEP) within a suitable cell line.

A preferred embodiment of the present invention comprises a PEP having at least one cysteine residue, which can form a disulfide bond with another PEP. A most preferred embodiment comprises a PEP dimer joined by such a disulfide bridge.

Another embodiment of the present invention includes a synthetic peptide, having at least 22 amino acids corresponding to residues 37 to 58 of IL-2. A most preferred embodiment includes an amino acid sequence at least 37 amino acids long, corresponding to SEQ ID NO: 1.

Other versions of the invention comprise a conjugate or a fusion protein, wherein the delivery vehicle is a tumor specific monoclonal antibody. Preferred versions of the invention include conjugates and fusion proteins, wherein the delivery vehicle is selected from the group consisting of a murine antibody, a human antibody, and a chimera of human and murine antibodies. The most preferred embodiments include a monoclonal antibody selected from the group consisting of Lym-1, Lym-2, TNT-1, TNT-2, and TV-1.

The conjugates and fusion proteins of the present invention can be used in a method for the therapy of neoplastic tissue. The therapeutic method comprises administering an effective amount of a conjugate or fusion protein to a tumor-bearing host. The therapy further comprises administering an antineoplastic therapeutic agent, after or at the same time as the administration of conjugate or fusion protein. Such a therapeutic method can improve uptake of an antineoplastic agent at a tumor site. A kit for use during the therapeutic method, contains either a vasoactive conjugate or fusion protein, and an antineoplastic agent.

In a similar manner, the vasoactive conjugates and fusion proteins of the present invention can be used in a diagnostic method of tumor imaging. The method comprises administering an effective amount of a vasoactive conjugate or fusion protein to a tumor-bearing host. The method further comprises administering a tumor imaging agent, after or at the same time as the administration of conjugate or fusion protein. The diagnostic method can increase the amount of a tumor imaging agent that accumulates at a tumor site. A diagnostic kit for use in the tumor imaging procedure contains either a vasoactive conjugate or fusion protein, and an appropriate tumor imaging agent.

BRIEF DESCRIPTION OF THE DRAWINGS

These and other features, aspects, and advantages of the present invention will become better understood with regard to the following description, appended claims, and accompanying drawings where:

FIG. 1 (A) shows the amino acid and DNA sequence of PEP (aa22–58)

FIGS. 2A and 2B show a schematic diagram of the chemical production of a permeability enhancing peptide (PEP) (A) dimer and (B) monomer;

FIGS. 3A and 3B show the results of biodistribution studies with recombinant human IL-2 (rhIL-2) and PEP immunoconjugates in tumor-bearing nude mice, wherein the results are expressed as either (A) % injected dose/gram or (B) tumor/organ ratios, (n=4)

DETAILED DESCRIPTION

This invention provides an active IL-2 peptide, preferably synthetic, and its dimer which have vasopermeability activity but which are devoid of cytokine activity. The invention also provides potent vasoactive immunoconjugates of these peptides with tumor-specific antibodies. Such conjugates facilitate the delivery of therapeutic and diagnostic agents in tumors and other tissues.

Permeability Enhancing Peptides

The invention provides vasoactive IL-2 peptides, preferably free of cytokine activity. These novel peptides include portions of the amino acid sequence of IL-2, sequences which can also be deduced from the nucleotide sequence, described by Taniguchi et al. (*Nature* 302: 305–310 (1983)), incorporated herein by reference. The peptides are preferably synthetic. The monomeric peptides can also be isolated from naturally occurring IL-2 by known techniques.

A series of distinct permeability enhancing peptides (PEP) have been synthesized which, when linked to an appropriate delivery vehicle, are responsible for increased vascular permeability in vivo. Moreover, the unprotected synthetic peptides by themselves are. short-lived after intravenous administration and have negligible effects on vascular permeability relative to unaltered IL-2. Consequently, the vasoactive peptide must be joined to an appropriate delivery vehicle to maximize the vasopermeablity effects of the peptides. Preferably, the peptides, alone or joined to a delivery vehicle, exhibit negligible cytokine activity in IL-2 bioassays, such as T-cell proliferation and cytotoxicity assays. Taken together, these characteristics of the PEP provide for a powerful vasoactive agent when linked to an appropriate delivery vehicle, but minimize any potential toxic effects on normal tissues.

The length of the PEP is preferably at least about 22 amino acids in length and most preferably about 37 amino acids in length. Preferred embodiments of the peptide include amino acids residue numbers 37 to 58, 33 to 58, or 37 to 72 of amino acid sequence SEQ ID NO: 1. These preferred embodiments exhibit about 50% of the vasopermeability effects of an IL-2 immunoconjugate when joined to an appropriate delivery vehicle. The most preferred embodiment of PEP comprises residue numbers 22 to 58, i.e., the entire amino acid sequence of SEQ ID NO: 1. This PEP embodiment exhibits an optimum of about 100% of the vasopermeability of an IL-2 immunoconjugate, when joined to an appropriate delivery vehicle.

Figure 1B:
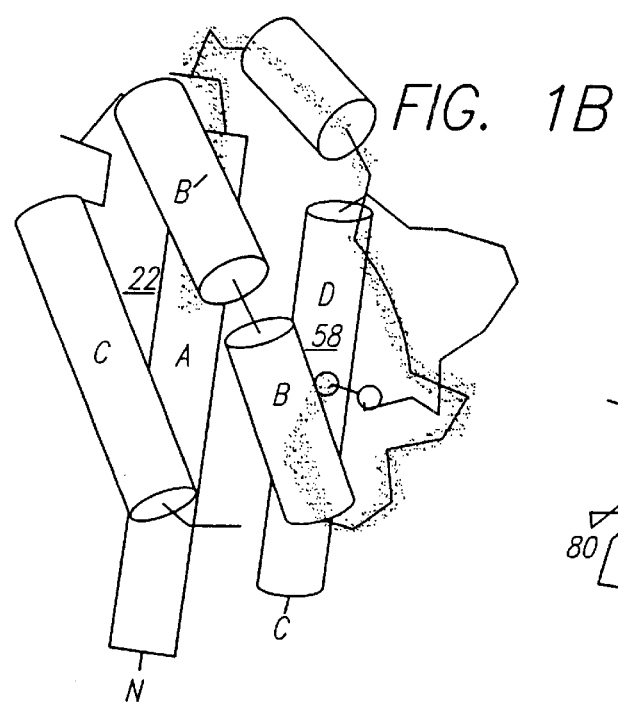
FIG. 1(B) shows a schematic drawing of IL-2 where helices are shown as cylinders (McKay, D. B., (1992))
Figure 1C:
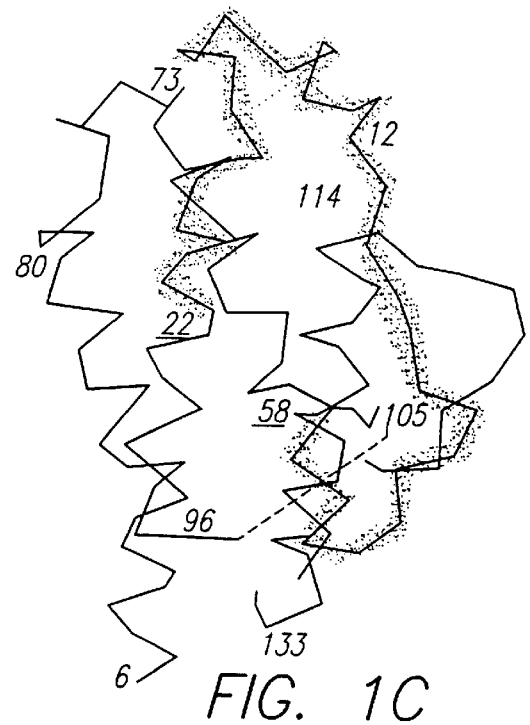
FIG. 1(C) shows a stereogram of a Cα atom backbone trace of one IL-2 molecule (McKay, D. B., (1992))
Figure 1D:
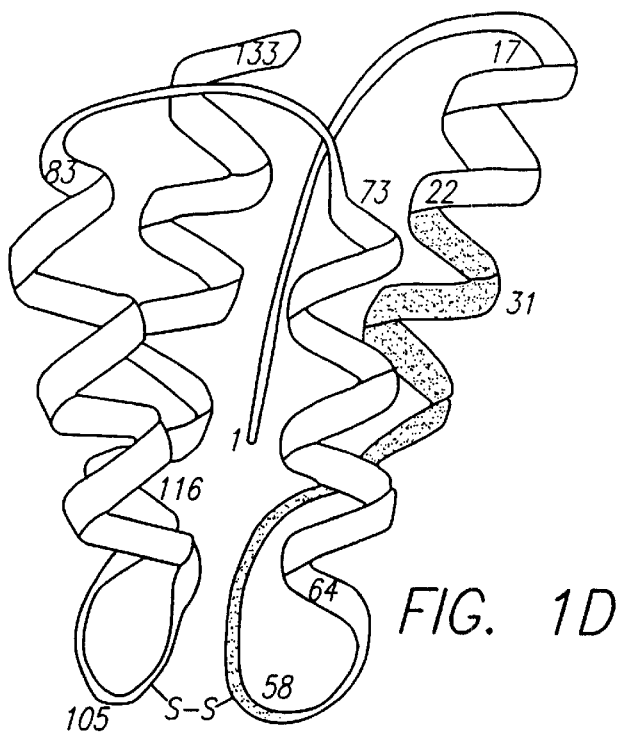
FIG. 1(D) shows a ribbon diagram of a member of the right-handed cylinder family of predicted IL-2 structure (Cohen et al., (1986)), wherein the PEP sequence is highlighted and the disulfide bond is shown in FIGS. 1(B), 1(C), and 1(D)

The complete amino acid sequence of the IL-2 peptide fragment that is the most preferred PEP (SEQ ID NO: 1), as well as the corresponding DNA sequence (SEQ ID NO: 2), is shown in FIG. 1A. The location of this fragment in the intact IL-2 molecule is shown schematically in three diagrams, which have been used by investigators to represent the IL-2 molecule (see FIGS. 1B, 1C, and 1D).

The permeability effects of the peptides of the present invention are further optimized when the PEP comprises a dimer, preferably linked by a disulfide bond. Consequently, a preferred embodiment of the PEP includes a cysteine residue and is capable of forming a disulfide bridge with another PEP molecule. A most preferred embodiment comprises a PEP dimer, having a disulfide bridge connecting two cysteine residues.

The PEP molecules acquire their ability to produce a localized increase in vascular permeability when they are joined to delivery vehicles, which can direct the vasoactive peptides to appropriate tumor targets. The joining of PEP with appropriate delivery vehicles, such as tumor-specific monoclonal antibodies (MAb), can be readily accomplished by chemical conjugation means, as described below.

Alternatively, the PEP can be joined to the tumor-specific MAb using genetic engineering methods to give a PEP/MAb fusion protein, also described below. In addition to the PEP, the conjugates or fusion proteins may include appropriate linker molecules, e.g. peptides or bifunctional reagents, which may overcome perturbations of the PEP or MAb's tertiary structure.

The permeability enhancing properties of the conjugates can be determined by in vivo experiments, such as those described in Example 7. Exemplary in vitro assays for cytokine activity are found in Example 8.

Selection of Delivery Vehicles

An important aspect of the invention comprises the potency of a vasoactive peptide when linked to a tumor-specific delivery vehicle. MAbs are ideal delivery vehicles because they are homogeneous, recognize specific determinants, and are relatively biocompatible. Preferred delivery vehicles include MAbs of mouse, rabbit, or other mammalian species of origin. Most preferably, the immunogenicity of non-human MAbs is avoided by the selection of human or human-mouse chimeric MAbs as delivery vehicles.

Suitable monoclonal antibodies (MAbs) for use in the invention comprise not only those having a specificity for antigens unique to tumor cells, but also those having a shared specificity for antigens of normal tissues. The essential property of these monoclonal antibodies is their effectiveness as carriers, which preferentially concentrate vasoactive agents at the site of the tumor. Suitable monoclonal antibodies are those having a specificity to antigens that are either more abundant or more easily bound in tumor tissue than in normal tissue.

Some MAbs against tumor or normal cellular antigens, suitable for use in the immunoconjugates are available commercially (e.g., Centocor, Malvern, Pa.).

Others may be prepared by the well-established hybridoma procedure of Kohler and Milstein (*Nature* 256: 495 (1975)), and commercial kits facilitate this process, e.g. HyBRL Prep Kit (Bethesda Research Labs, Bethesda Research Labs, Bethesda, Md.).

The selection of hybridoma cell lines producing suitable MAbs is accomplished by first growing hybridoma cells for several days, for example, in the wells of microtiter plates. Cell supernatants are then tested for the presence of MAb to tumor or cellular antigens by any convenient immunoassay, for example, an ELISA. Cells testing positive are then expanded into larger scale cultures to produce larger quantities of MAbs. An adequate amount of MAb can then be purified from the supernatants, for example, using Protein A affinity chromatography.

In a preferred embodiment of the invention, commercially available MAbs specific for lymphoma cells, e.g., Lym-1 and Lym-2, are used (Techniclone, Corp., Tustin, Calif.).

In another preferred embodiment, MAbs specific for intracellular antigens accessible in degenerating cells, e.g. TNT-1 and TNT-2 are used (Techniclone, Corp., Tustin, Calif.).

In yet another preferred embodiment, MAbs specific for tumor vessels, e.g. TV-1 (Epstein, A. L, *Cancer Res.* 55: 2673–2680 (1995), incorporated herein by reference) are used.

The MAb of the immunoconjugate may be either intact whole antibody, the monovalent HL isoform, the F(ab')2 portion of antibody, or Fab antibody fragments. Removal of all or part of the Fc portion of the antibody molecule can facilitate it use by removing sites or domains which interact with non-tumor components such as Fc receptors or complement while leaving the antigen binding sites intact. Antibody fragments like Fab, HL, and F(ab')2, which have ⅓, ½, and ⅔ the weight of whole antibody, respectively, are better able to diffuse through the interstitial tissue and into the tumor. However, the Fab, HL, and F(ab')2 fragments are cleared from the circulation more rapidly. Fab fragments may be prepared by digestion of whole antibody with papain, or digestion of whole antibody with pepsin to give F(ab')2 fragments, followed by digestion of interchain disulfide bonds to yield univalent fragments.

In addition, suitable delivery vehicles should retain their ability to bind with antigen following chemical conjugation with vasoactive peptides. The immunoreactivity of MAbs, before and after conjugation with peptides, can be determined by any suitable immunoassay, such as the radioimmunoassay described in Example 6. Preferably, immunoconjugates having greater than 75% immunoreactivity, as compared to the unconjugated antibody, are used in vivo.

Chemical Conjugation Methods

The structural link between the MAb and the vasoactive peptide, as well as the chemical method by which they are joined, should be chosen so that the binding ability of the MAb and the biological activity of the peptide, when joined in the conjugate, are minimally compromised. As will be appreciated by those skilled in the art, there are a number of suitable chemical conjugation methods, including the following procedures.

1. Conjugation by the CDI Method

Carbodiimides (CDIs), which are anhydrides of urea, can produce cross-links between the antibody and the peptide, regardless of either molecule's orientation. Conjugants are derived by condensation of the antibody and peptide under acidic conditions with CDI. This method provides a rapid and simple means of conjugation.

2. Conjugation by the SPDP Method

N-succinimidyl 3-(2-pyridyldithio) propionate (SPDP) is a heterobifunctional reagent which introduces thiol groups to the terminal amino of proteins, and has been used in a number of immunoconjugates.

3. Conjugation by the SMCC Method

Peptides can also be coupled to antibodies using the bifunctional reagent, succinimidyl-4-(N-maleimido methyl) cyclohexane 1-carboxylate (SMCC).

4. Conjugation by the NHS Method

N-hydroxisuccinimide (NHS) activates a terminal COOH group, for example, of a peptide, to form an active ester derivative that can be covalently coupled to the protein of the monoclonal antibody.

5. Glutaraldehyde

An alternative method for the conjugation of peptides to proteins uses glutaraldehyde as a reagent for coupling. Nucleophilic groups such as sulfhydryl and amino groups covalently add to the aldehyde forming a Schiff base. Excess active glutaraldehyde groups can be subsequently blocked by addition of glycine, and the excess peptide and glycine molecules removed by dialysis.

Genetically Engineered Fusion Proteins

Genetically engineered fusion proteins, constructed by cloning the gene sequences of antibody light chains and heavy chains fused to sequences encoding vasoactive peptides, present an attractive alternative to the chemical linkage of vasoactive peptides to MAbs. These constructs can be tailored to be less immunogenic than MAbs from non-human sources. Moreover, fusion proteins allow defined molar amounts of PEP monomer or, alternatively, at least two tandemly linked PEP sequences, to be attached at specific sites of the MAb.

As an example, mRNA from hybridoma cells expressing a monoclonal antibody is isolated. From this mRNA, cDNA is reverse transcribed and amplified by polymerase chain reaction. Specific regions encoding heavy and light chains of an immunoglobulin, e.g. variable and/or constant regions, can be amplified by the selection of appropriate oligonucleotide primers targeting the desired region(s). The cDNA is sequenced, mapped by restriction endonucleases, and cloned into an appropriate transfer vector. At a minimum, the immunoglobulin sequences encoding an antigen binding domain, i.e. the variable light chain and variable heavy chain regions, are contained in the transfer vector. In addition, a truncated or full length portion of the constant region encoding the original or another immunoglobin can be joined in frame with the variable region, to allow expression of the joined regions. For example, a preferred embodiment of the invention encodes a chimeric MAb, comprised of murine variable regions linked to their corresponding human constant regions of the heavy and light chains.

An appropriate DNA sequence, encoding at least one vasoactive peptide, is then ligated proximate to a region of an immunoglobulin gene encoding the carboxy-terminus, preferably a constant region, most preferably the constant region of a heavy chain. The best site for attachment for each vasoactive peptide may be different and may be easily determined via experimental methods. For example, none or various lengths of amino acid encoding linkers may be inserted between the PEP and the carboxy-terminus of the immunoglobulin gene. In addition, two or more tandemly linked PEP sequences can be joined to the appropriate region(s) of an immunoglobulin gene. The resulting expression products can then be tested for biologic activity.

The completed engineered gene for the fusion protein is inserted into an expression vector, which can be introduced into eukaryotic or prokaryotic cells by gene transfection methods, e.g. electroporation or the calcium phosphate method. The fusion protein product can then be expressed in large scale cell culture and purified.

Use of Vasoactive Peptides

A successful vasoactive immunoconjugate or fusion protein will maximize the clinical effectiveness of monoclonal antibody-based diagnosis and therapy. Clinically, the vasoactive immunoconjugate or fusion protein is given before or with an intravenously injected immunodiagnostic, chemotherapeutic, or immunotherapeutic agent. Induction of a localized permeability change within the tumor vasculature will make the tumor more susceptible to penetration and improve the delivery of drugs, toxins, radioisotopes, monoclonal antibodies, or conjugates of monoclonal antibodies with drugs, toxins, or radioisotopes to the tumor site.

The suitability of tumor specific antibodies, immunoconjugates, and genetically engineered fusion proteins for use in vivo is determined by their biodistribution, cellular localization, selective binding, and rate of clearance from the tumor host, or an animal model of the tumor host. Studies to asses this suitability are conveniently carried out by means of labeled MAbs. For example, radioiodination of antibody moieties can be accomplished by the modified chloramine T method of Example 6. A tumor host is treated with immunoconjugate, a fusion protein, or left untreated. After injecting a tumor host with the labeled MAb, the effectiveness of a vasoactive conjugate or fusion protein can be evaluated by appropriate radioimaging, biodistribution, histological studies, and autoradiographic methods.

The time required to produce the maximum vasoactive effect depends on the specific conjugate or fusion protein chosen. However, an optimal interval between the time of administering the vasoactive agent and the therapeutic or diagnostic agent can be determined experimentally. For example, the ability of a radiolabelled MAb to concentrate selectively at a tumor site can be determined by radioimaging. Posterior gamma scintillation images (100,000 cpm) are obtained from an anesthetized host on alternate days after injection of radiolabeled MAb, using a gamma scintillation camera with a pinhole collimator. The camera is preferably interfaced with a computer system. An appropriate $^{131}I$ standard with the same activity is counted to quantitate the data.

Further biodistribution studies can be performed using animal models, wherein the host animal is sacrificed at an optimal time, as determined by the imaging studies described above. Blood, major organs and tumor tissues are then excised, weighed, and counted to determine the biodistribution of the MAb. In addition, tumor tissue can be fixed and embedded, and tissue sections examined by autoradiography to determine the location of the bound radiolabeled MAb in the tumor.

It is anticipated that the minimum time between the administration of the vasoactive conjugate or fusion protein and the administration of a diagnostic or therapeutic agent is at least about 20 minutes, and the maximum time is about 72 hours.

The dose of vasoactive immunoconjugate or fusion protein to be given is based on criteria of medical judgment and experience, both objective and subjective. However, an adequate measure of an effective dose is that amount which improves the clinical efficacy of therapy, or accuracy of diagnosis, to a statistically significant degree. Comparisons can be made between treated and untreated tumor hosts to whom equivalent doses of the diagnostic or therapeutic agents are administered. Where a diagnostic or therapeutic agent is toxic to normal tissue, an effective dose of vasoactive conjugate or fusion protein is one which minimizes such toxic effects.

A preferred therapeutic agent is a clinically useful Mab. In addition, an antineoplastic therapeutic agent can be a tumoricidal agent, such as a radioisotope, a chemotherapeutic drug, or a toxin. Moreover, the MAb can be attached to a tumoricidal agent, e.g., radioisotope, chemotherapeutic drug, or toxin.

A diagnostic agent can be used for tumor imaging and is comprised of a MAb having a specificity for a tumor, which has a label detectable in vivo. Preferably, this label comprises a radioactive isotope. In addition to the detectable label, the tumor imaging agent can also be attached to a cytotoxic agent, such as a radioisotope, drug, or toxin.

In another version of the invention, the vasoactive immunoconjugate or fusion protein is linked to a tumoricidal agent. Consequently, the therapeutic method is a simplified procedure comprised of administering to a tumor bearing host an effective amount of a vasoactive conjugate or fusion protein, which is linked to a chemotherapeutic agent, toxin, or radioisotope.

Similarly, the vasoactive immunoconjugate or fusion protein can be linked directly to a detectable label, such as a radioisotope. Consequently, the diagnostic method can comprise simply administering to a tumor bearing host the labeled vasoactive immunoconjugate in an amount sufficient to give a clear tumor image.

The previous versions of the present invention have many advantages including the ability to increase vascular permeability at the site of neoplastic or other diseased tissue. Moreover, the previous versions of the invention provide potent vasoactive agents that enhance the uptake of therapeutic and diagnostic agents at a tumor site with a minimum of toxic side effects on normal tissues.

EXAMPLES

Reagents

All chemicals, such as N-hydroxysuccinimide (sulfo-NHS), 1-cyclohexy-3-(morpholinoethyl)carbodiimide metho-p-toluenesulfonate (CDI), and chloramine T were purchased from Sigma Chemical Co. (St. Louis, Mo.). Iodo-beads were purchased from Pierce (Rockford, Ill.). All solvents were of analytical grade and were used as purchased. Iodine-125 was obtained as sodium iodide in 0.05 N sodium hydroxide solution (ICN Biomedicals, Irvine, Calif.). Radioactive samples were measured using either a 1282 Compugamma counter (LKB Instruments, Pleasant Hill, Calif.) or a CRC-7 dose calibrator (Capintec Inc., Pittsburgh, Pa.).

Murine monoclonal antibodies Lym-1 ($IgG_{2a}$) and TNT-1 ($IgG_{2a}$) were obtained from Techniclone, Corp. (Tustin, Calif.). Lym-1 is directed against a variant of the HLA-Dr antigen expressed on the cell surface of human B-lymphocytes and malignant lymphomas (Epstein, A. L., et al., Cancer Res. 47: 830–840 (1987)), whereas TNT-1 recognizes an epitope of nucleohistones expressed in the nucleus of mammalian cells (Epstein, A. L., et al., Cancer Res. 48: 5842–5848 (1988)). Protein concentrations of the antibody preparations were estimated by optical spectroscopy at 280 nm. Recombinant human IL-2 (rhIL-2) was obtained from Hoffman La-Roche (Nutley, N.J.) or Chiron (Emeryville, Calif.). Human serum albumin (HSA) was obtained from Sigma Chemical Company.

For in vivo experiments, the Raji Burkitt's lymphoma cell line and the ME-180 human cervical carcinoma cell line were used as previously described (Chen, F.-M., et al., J. Nucl. Med. 31: 1059–1066 (1990)). Both cell lines were grown in RPMI-1640 medium containing 10% fetal calf serum (Hyclone Laboratories, Logan, Utah), penicillin G (100 U/ml), and streptomycin sulfate (100 µg/ml). For in vitro cytotoxicity studies, the K562 human erythroleukemia cell line, the Daudi Burkitt's lymphoma cell line, and the mouse P815 mastocytoma cell line were used. All of the cell lines were cultured in a 37° C. well-humidified 5% $CO_2$ incubator and were routinely passaged twice weekly.

Example 1

Synthesis of Human IL-2 Peptide Fragments

Peptides were synthesized by the Merrifield method (Merrifield, B., Science 232: 341–347 (1986)) using a one-column peptide synthesizer (Model 430A, Applied Biosystems, Foster City, Calif.). The protected peptides were assembled by solid-phase synthesis and cleaved by trifluoroacetic acid (Fields, C. G., et al., Peptide Res. 4: 95–101 (1991); King, D. S., et al., Int. J. Peptide Prot. Res. 36: 255–266 (1990)). The peptides were then purified by gel filtration on Sephadex G-10 in 30% acetic acid and lyophilized. A list of the different peptide fragments of IL-2 generated by these procedures is provided in Table 1 (see below).

Example 2

Conjugation of Recombinant IL-2 to Tumor-Specific Monoclonal Antibody

Recombinant IL-2 was radio-iodinated and used in trace amounts during subsequent coupling reactions to ascertain the binding of IL-2 to antibody or HSA. Lyophilized IL-2 was dissolved in sufficient water to give a final concentration of 2 mg/ml. Fifty µl of IL-2 solution (100 µg), 100 µCi of carrier free iodine-125 and 5 µl of chloramine T (10 mg/ml) in water were added to 100 µl in 0.1 M phosphate buffer, pH 7.4, and the reaction was allowed to proceed for 1 min at room temperature. The reaction was quenched with 100 µl of anion exchange resin (AG1=X8; Bio-Rad Laboratories, Richmond, Calif.) in PBS. After 1 min the suspension was withdrawn and filtered in a Spin-X centrifuge unit (Costar, Cambridge, Mass.) to remove the resin.

The coupling reaction was initiated by the addition of 500 µl of IL-2 (2 mg/ml) to 500 µl of antibody (10 mg/ml), CDI (14 mg), and sulfo-NHS (8 mg) to give a total volume of 1.2 ml in 0.1 M phosphate buffer, pH 7.4. The reaction was incubated overnight at 4° C. After centrifugation, the soluble coupled antibody was chromatographed on a Sephadex G-100 column calibrated with blue dextran. The radioactivity and antibody peaks co-eluted indicating the IL-2 had attached to the antibody. From the antibody concentration and radioactivity, approximately one molecule of IL-2 was calculated to be bound to each antibody molecule. These immunoconjugates retained a minimum of 75% of the antibody binding reactivity as determined by a live cell binding assay (Epstein et al.,(1987); Gaffar, S. A., et al., *J. Immunoassay* 12: 1–4 (1991)).

Example 3

Conjugation of IL-2 Peptide Fragments to Antibody and Human Serum Albumin

Portions of the IL-2 peptide fragments, prepared according to Example 1, were also radio-iodinated prior to conjugation with antibody or HSA using a slightly different procedure. Lyophilized peptide fragments were dissolved in 10% aqueous ethanol to a final concentration of 1 mg/ml. One hundred µl of this solution was added to a solution of 100 µCi of Na$^{125}$I in 0.1 N NaOH neutralized with an equivalent volume in 0.1 M acetic acid. The mixture was stirred vigorously and two iodo-beads were added. The reaction was allowed to proceed for 1 hr. After incubation the mixture was withdrawn into a syringe, and the iodo-beads were washed twice with 100% aqueous ethanol. Combined wash liquids were purified on a short Sephadex G-10 column (eluted with PBS, pH 7.4).

The purity of the radiolabeled fragments was determined by analytical instant thin layer chromatography (ITLC). ITLC strips (2×20 cm) having silica gel impregnated fibers (No. 61886, Gelman Sciences, Ann Arbor, Mich), were activated by heating at 110° C. for 15 min prior to use, spotted with 1 µl of sample, air dried, cut in half, and counted to determine fragment bound and unbound radioactivity. In this system, free iodine migrates with the solvent, while labeled peptide fragments remain near the origin. In all cases, greater than 90% of the radioactivity was associated with the IL-2 peptide fragments. The different radiolabeled IL-2 fragments were used in trace amounts in the reaction mixture to ascertain the binding of peptide fragments to the antibody, as noted below. coupling reactions were initiated by adding different peptide fragments to the antibody or HSA, CDI, and sulfo-NHS in a 1:2:50:50 ratio by weight to give a total volume of 0.6 ml in 0.1 M phosphate buffer, pH 7.4. The reactions were incubated overnight at 4° C. After centrifugation, the soluble coupled antibody was chromatographed on a G-100 column calibrated with blue dextran. From the antibody concentration and radioactivity, approximately one-half molecule of IL-2 peptide fragment was calculated to be bound to each antibody or HSA molecule.

An alternative method used for the conjugation of peptides to proteins used glutaraldehyde as a reagent for coupling. Nucleophilic groups such as sulfhydryl and amino groups covalently add to the aldehyde forming a Schiff base. Two mg of protein (10 mg/ml in PBS, pH 8.0) were mixed with 2–3 mg peptide (5 mg/ml in H$_2$O) at room temperature. The pH was maintained at 8.0 with the addition of dilute NaOH. One hundred µl of a 0.02% solution of fresh glutaraldehyde was added to the reaction mixture with mixing over 9–10 min, and the mixture stored overnight at 4° C. The remaining active glutaraldehyde groups were blocked by addition of 0.2 M glycine (0.2 ml) for 2 hr. The excess peptide and glycine molecules were removed by dialysis.

Conjugated peptide fragments were analyzed by fast protein liquid chromatography (FPLC) performed at room temperature using a Pharmacia system (Pharmacia, Piscataway, N.J.) equipped with two P-500 solvent pumps, a MV-8 motor valve injector, a single path UV monitor, a LLC-500 automated controller, and an REC-482 dual pen chart recorder. The conjugates were eluted from a superose-12 HR 10/30 pre-packed column (Pharmacia), using 0.1 M PBS, pH 7.2 as the solvent system, at a flow rate of 1.0 ml/min. The UV absorbance of the FPLC eluate was detected at 280 nm. The conjugated antibodies appeared at 650 seconds and the unbound fragments at 1170 seconds. Immunoconjugates retained a minimum of 75% of the antibody binding reactivity as determined by an indirect cell binding assay (Epstein et al.,(1987); Gaffar et al.(1991)).

Example 4

Conjugation of PEP Dimer to Antibody

The PEP dimer was prepared by linking the monovalent peptide through the intrinsic cysteine (amino acid #58), to form a disulfide bond as shown diagrammatically in FIG. 2A. The thiol form of PEP was regenerated by treatment with 10 mM 2-mercaptoethylamine for 30 min, followed by gel filtration on a Sephadex G-10 column equilibrated with 0.1 M sodium phosphate, pH 6.8. The peptide was then incubated for 16 hr at room temperature at pH 9 by the addition of 5 M NaOH (FIG. 2). The desired peptide dimer was purified from the reaction mixture by gel filtration on a Sephadex G-25 column equilibrated with phosphate buffer, pH 7.4. Yields of 90% PEP dimer were found under those conditions without the formation of high molecular weight species. The PEP dimer was coupled to antibody using the conditions described above and was found to have approximately the same conjugation yield as the other peptides.

Example 5

Conjugation of PEP-Phenylmaleimide Monomer to Antibody

1. Synthesis of N-phenylmaleimide

The approach to synthesizing N-phenylmaleimide is shown schematically in FIG. 2B. Maleic anhydride (1.33 g, 13.6 mmol) was dissolved in toluene (15 ml) and aniline (1.3 g, 13.9 mmol) in toluene (20 ml) was added dropwise over a 20 min period. The reaction mixture was stirred for 45 min at room temperature and then cooled in an ice-water bath. The precipitated product, N-phenylmaleamic acid, was collected by filtration, washed with hexane and dried overnight (2.1 g yield).

Proton ($^1$H)nuclear magnetic resonance (NMR) analysis of the product was recorded on a Hitachi Perkin-Elmer R-24 60 MHz instrument. NMR sample concentrations were about 10% (w/v) in the indicated solvent. Chemical shifts (ppm) are reported down field ($\delta$) relative to the internal tetramethylsilane (TMS) standard. The following results verified that the product was N-phenylmaleamic acid: $^1$H NMR (Me$_2$S0-d$_6$, $\delta$); 10.3 (1H, singlet, OH), 7–7.8 (5H, multiplets, 5 aryl CH), 6.4 (2H, doublet of doublets, COCH=CHCO).

N-phenylmaleamic acid (2.0 g, 10 mmol) was added and the solution stirred at 120° C. The brown precipitate was filtered and evaporated to dryness under reduced pressure and the residue was dissolved in diethyl ether. The ether mixture was filtered and the filtrate was again evaporated to dryness. The residue obtained was applied to a flash chromatography column (30×200 mm) of Kieselgel 60, 230–400 mesh (No. 9385, E. Merck, Darmstadt, Germany). Elution with 500 ml of ethyl acetate/hexane (1:3) yielded fifty fractions. Fractions 25–40 were combined to provide pure N-phenylmaleimide (1.5 g yield): TLC (EtOAc/hexane, 1:3) R$_f$ 0.45. $^1$ NMR (CDCL$_3$, $\delta$): 7–7.8 (5H, multiplets, 5 aryl CH); 6.8 (2H, singlet, COCH=CHCO).

Product isolation and identification was conducted by high performance liquid chromatography (HPLC) using a Beckman System Gold Instrument (Beckman Instruments Inc., Fullerton, Calif.) equipped with two 110B solvent pumps, a 210A injector valve, a 166 programmable absorbance detector, and a 406 analog interface module. A Zorbax GF-250 reversed-phase column (DuPont, Wilmington, Del.) was eluted at a flow rate of 1 ml/min with 100% acetonitrile. Peak detection was determined by UV absorbance at 254 nm. The starting material, N-phenylmaleamic acid, appeared at 220 seconds followed by the desired product at 340 seconds.

2. Reaction of PEP with N-phenylmaleimide and Formation of the Immunoconjugate

The conjugation of N-phenylmaleimide to the PEP was accomplished by the addition of a 2.5-fold molar excess of N-phenylmaleimide (in 15 $\mu$l methanol) to PEP dissolved in 0.1 M citrate buffer, pH 6.0. The reaction was allowed to proceed for 30 min at 37° C. The reaction mixture containing the PEP-phenylmaleimide conjugate was exposed to 15 mM mercaptoethylamine to reduce any disulfide bonds that might have formed during the reaction and left to react overnight. The final reaction conjugate was purified by gel filtration on a Sephadex G-10 column which was eluted with 0.01 M PBS, pH 7.2. As with the dimer, coupling of the PEP-phenylmaleimide monomer to the antibody was performed as described above and produced approximately the same conjugation yield.

Example 6

Preparation and Analysis of Monoclonal Antibodies

1. Radioiodination of Antibodies

F(ab')2 fragments of Lym-1 and TNT-1 monoclonal antibodies were radiolabeled with iodine-125 using a modified chloramine T method. Briefly, the iodination reaction was initiated by adding chloramine T at a weight ratio of 10:1 (antibody:chloramine T). The reaction was quenched by the addition of sodium metabisulfite, and the mixture was chromatographed on a Sephadex G-25 gel column that was previously equilibrated with PBS containing 1% bovine serum albumin (Sigma). Fractions of $^{125}$I-labeled monoclonal antibodies were collected and diluted with the same buffer to an appropriate volume for injection.

Radiolabeled antibodies were analyzed using an analytical ITLC system as described in Example 3. All preparations revealed the same radiochemical purity ($\geq$98%).

2. Immunoreactivity of Radiolabeled Monoclonal Antibodies

The immunoreactivity of radiolabeled Lym-1 preparations was monitored by a live cell radioimmunoassay. Raji cells were washed twice in cold PBS containing 1 mg/ml bovine serum albumin and 0.02% sodium azide. Cells (5×105) resuspended in 100 $\mu$l of wash buffer were pipetted into microtiter wells (Immulon Removawell Strips; Dynatech Labs, Inc., Alexandria, Va.). The microtiter plates were pre-treated the previous night with BSA (10 mg/ml) in PBS with azide in order to prevent the antibody solutions from binding to the wells. Radiolabeled Lym-1 or Lym-1 immunoconjugates were then added (100,000 cpm/well) in a volume of 100 $\mu$l/well and the plates were incubated for 30 min at room temperature with constant shaking. The plates were then washed 4 times by spinning at 1,000 rpm for 5 min, and aspirating the supernatants with a 12-tip micromatic manifold, and then resuspending the cells in 200 $\mu$l of wash buffer using a Titertek Multichannel pipet (Flow Labs, McLean, Va.). The wells were then separated mechanically and counted in a gamma counter to quantitate the amount of label binding to the cells.

Approximately 80% of radiolabeled Lym-1 F(ab')2 preparations were found to bind Raji cells by live cell radioimmunoassay. The radiolabeled TNT-1 F(ab')2 had an immunoreactivity of $\geq$80% in a paraformaldehyde-acetone-treated cell assay developed in our laboratory (Gaffar et al., (1991)).

Example 7

In Vivo Vasopermeability Studies

1. Tumor Models and Biodistribution Studies

TNT-1 immunoconjugates were tested in the ME-180 human cervical carcinoma system to demonstrate targeting of TNT-1 immunoconjugates to intracellular antigens accessible in permeable (dead) tumor cells. The ME-180 human cervical carcinoma cell line was heterotransplanted in the left thigh of 6-week old female athymic nude mice (Harlan Sprague Dawley, San Diego, Calif.) by the subcutaneous injection of a 0.2 ml inoculum consisting of 10$^7$ cells. The tumors were grown for 3–4 weeks until they grew to approximately 1 cm in diameter.

Lym-1 immunoconjugates were tested in the Raji lymphoma model to demonstrate targeting cell-surface antigens. The Raji lymphoma cell line was used to produce heterotransplants in 6-week-old female nude mice by the subcutaneous injection of a 0.2 ml inoculum consisting of 4×10$^7$ Raji cells and 4×10$^6$ human fetal fibroblast feeder cells in the left thigh. Three days prior to injection, the mice were irradiated with 400 rads using a cesium irradiator to ensure a high take rate of the implanted cells. The tumors were grown for 14–18 days until they grew to approximately 1 cm in diameter.

To test the relative effects of the immunoconjugates on the biodistribution and tumor uptake of Lym-1 or TNT-1 in tumor-bearing mice, separate groups of 4–5 mice were given intravenous injections of 30 $\mu$g of antibody alone or antibody conjugate. At 2.5 hr after injection, each group received 50 $\mu$Ci of $^{125}$I-labeled Lym-1 or TNT-1 F(ab')$_2$ fragment as tracer.

All animals were sacrificed 72 hr later, by sodium pentobarbital overdose, for biodistribution analysis. Various organs, blood, and tumor were removed, weighed, and samples were counted in a gamma counter. For each mouse, data were expressed as tumor:organ ratio (cpm per gram tumor/cpm per gram organ) and percent injected dose/gram (%ID/g). From these data, the mean and the standard deviation were calculated for each group.

2. Identification of Vasoactive IL-2 Peptide Fragments

Based on the primary, secondary and tertiary structures of IL-2, a series of distinct peptides were synthesized in order to identify the sequences responsible for increased vascular permeability. The peptides and their sequences are listed in Table 1. Each peptide and rhIL-2, as well as their respective immunoconjugates with MAb Lym-1, were assayed for their ability to induce tumor vascular permeability and enhanced antibody uptake in Raji tumor-bearing nude mice.

TABLE 1

Vasopermeability Activity of Interleukin-2 Synthetic Peptide Fragments and Immunoconjugates

| Fragment/ Immunoconjugate[1] | Amino Acid Sequence | Vasopermeability (% Lym-1/IL-2) |
| --- | --- | --- |
| 3A | 44–58 | n.t.[2] |
| Lym-1/3A | | 0 |
| B1 | 37–58 | n.t |
| Lym-1/B1 | | 50 |
| 3B | 33–58 | n.t. |
| Lym-1/3B | | 50 |
| 3C | 22–58 | 0 |
| Lym-1/3C | | 100 |
| E6 | 22–38 | n.t |
| Lym-1/E6 | | 0 |
| A3 | 37–72 | n.t. |
| Lym-1/A3 | | 50 |
| 4A | 105–133 | n.t. |
| Lym-1/4A | | 0 |
| 4B | 87–133 | n.t |
| Lym-1/4B | | 0 |
| IL-2 | 1–133 | 75 |
| Lym-1/IL-2 | | 100 |

[1]30–40 pM of peptide were added per assay
[2]not tested

Control studies used intact IL-2 and the Lym-1/IL-2 immunoconjugate to establish markedly enhanced levels of Lym-1 uptake in Raji tumor bearing nude mice for comparison. As noted previously (LeBerthon et al. (1991)), enhanced permeability can be obtained despite the fact that chemically conjugated MAb/IL-2 does not demonstrate cytokine activity. As shown in Table 1, a vasoconjugate derived from one synthetic peptide, designated 3C, produced approximately 100% of the vasopermeability effects of Lym-1/IL-2 chemical conjugate. Three other vasoconjugates, composed of synthetic peptides 3B, B1, and A3, which contained smaller fragments of 3C, produced approximately half the vasopermeability effects of Lym-1/IL-2 in these assays.

As expected, intravenous administration of the unprotected and short-lived unconjugated synthetic fragments by themselves had no effect of Lym-1 uptake in tumor-bearing nude mice. Hence, conjugation of peptides to another macromolecule, such as an antibody, is required to demonstrate the biologic activity of the synthetic peptides. By comparison, native IL-2 had 75% vasopermeability in the in vivo model.

From the data presented in Table 1, it appears that the entire sequence of amino acids 22–58 produces optimal vasopermeability. However, conjugates composed of amino acids 37–58, 33–58, and 37–72 retain 50% of the activity, whereas fragment E6, consisting of amino acids 22–38, has no activity.

3. In vivo Analysis of PEP Immunoconiuqates

MAb alone, MAb/IL-2, or MAb/PEP immunoconjugates were used to pre-treat tumor-bearing nude mice in two tumor models in order to demonstrate increased tumor uptake of radiolabeled MAb 2.5 hours after pre-treatment. TNT-1 immunoconjugates were used in the ME-180 human cervical carcinoma system to demonstrate targeting to intracellular antigens accessible in permeable (dead) tumor cells. In complementary studies, Lym-1 immunoconjugates were used in the Raji lymphoma model to demonstrate targeting cell-surface antigens.

As shown in FIG. 3A, TNT-1 pre-treatment gave 1.28% of the injected dose in the tumor and TNT-1/IL-2 and TNT-1/PEP pre-treatments led to 4.5 and 4.4 percent injected dose/gram, respectively. Equally as impressive, pre-treatment with Lym-1 alone led to only 1.4% of the injected dose of radiolabeled Lym-1 accumulating in the tumor, while Lym-1/IL-2 and Lym-1/PEP gave 5.7 and 5.6 percent injected dose/gram, respectively (FIG. 4A). In both systems, there was an approximate four-fold increase in radiolabeled antibody within the tumor.

Figure 4B:
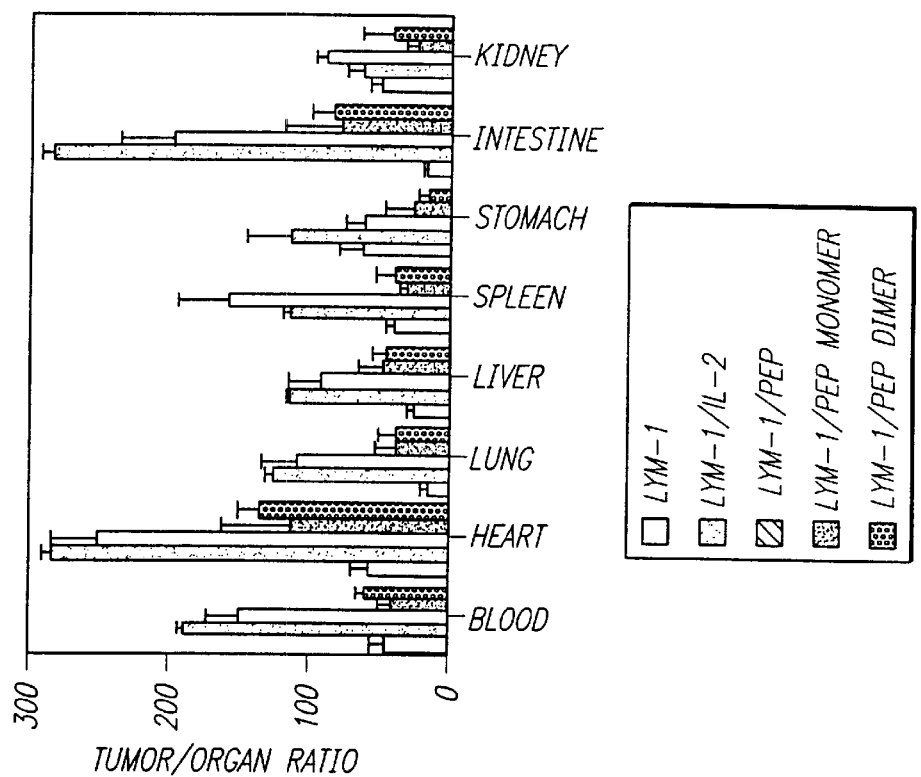
FIGS. 4A and 4B show the results of biodistribution studies with rhIL-2, PEP, PEP monomer, and PEP dimer immunoconjugates in tumor bearing nude mice, wherein the results are expressed as (A) % injected dose/gram and (B) tumor/organ ratios.
Figure 4A:
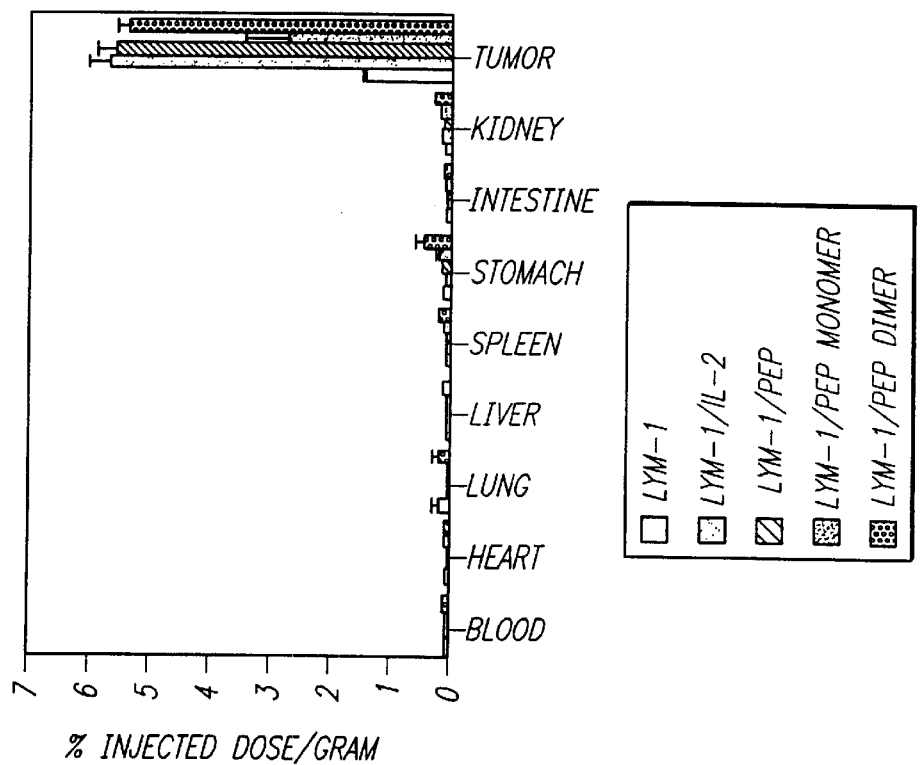

In addition to these findings, use of IL-2 or PEP immmunoconjugates increased the specific targeting of the radiolabeled antibodies as shown by the higher tumor/organ ratios (FIGS. 4A and 4B).

These results indicate that PEP is equivalent to rhIL-2 after conjugation to two different monoclonal antibodies for the enhancement of antibody uptake in tumor. Unlike IL-2, however, unconjugated PEP, which has a molecular weight of 3,700 Daltons, showed no vasopermeability activity after intravenous administration in the mouse (Table 1), presumably because of its rapid degradation and clearance from the circulation.

4. In vivo Evaluation of PEP monomer and Dimer Immunoconjugates

The presence of the terminal cysteine (amino acid #58) suggests that dimerization of the synthetic peptide might be occurring during the conjugation procedures. In order to assess whether dimerization affected the vasopermeability effects of PEP, monomer and dimer forms of PEP were produced before conjugation as described in Example 5 and summarized in FIG. 2. Vasoconjugates constructed with these chemically-generated fragments were therefore composed of only monomer or dimer forms of PEP for comparative purposes.

When used as a pre-treatment in tumor-bearing nude mice, biodistribution analysis demonstrated that the vasoconjugate consisting of the dimer had an approximately two-fold enhancement of antibody uptake in tumor compared to the vasoconjugate constructed with the PEP monomer (FIG. 4). In addition, the vasoconjugate constructed with the PEP dimer gave approximately the same enhancement in antibody uptake as the MAb/IL-2 conjugate, indicating that dimerization was important in the generation of optimal vasopermeability at the tumor site in this model system.

Example 8

Cytokine Studies

1. IL-2 Bioassays (Proliferation Assay)

The growth of an IL-2 dependent indicator cell line, CTLL-2, was used to compare the biologic activity of PEP, PEP conjugates, and positive control human recombinant IL-2. Samples of PEP, PEP conjugates, or IL-2 standards (100 μl/well) were serially diluted 3-fold from an initial concentration of 8.1 pM (recombinant IL-2) in sterile 96-well flat bottom microtiter plates. CTLL cells ($4\times10^5$) in a volume of 50 μl were added to each well. Plates were incubated for 18 hr in 5% $CO_2$ at 37° C., then pulsed with 0.5 μCi of $^3$H-thymidine for 6 hr (25 μl of a 1:50 dilution of 1.0 mCi in media; Amersham, Arlington Hts. Ill.) prior to harvesting wells onto glass fiber filter paper and liquid scintillation counting in glass minivials. While recombinant IL-2 was highly active as a positive control, none of the PEP-containing preparations were found to support the proliferation of the T cell line.

2. Cytotoxicity Assays

The ability of PEP and PEP conjugates to induce LAK cell killing was tested by $^{51}$Cr release microcytoxicity assays in 96-well microtiter plates as previously described (Katsanis, E., et al., *Blood* 78: 1286–1291 (1991). Two populations of effector cells were used, human peripheral blood mononuclear cells (PBMC) or murine splenocytes. The effector cells were isolated by Ficoll density gradient centrifugation and activated for 4 days in vitro in media containing 13.7 pM or 80 pM PEP, or 13.7 pM antibody/PEP or HSA/PEP conjugates at a density of $0.5\times10^6$ cells/ml. Freshly isolated effectors in media without human recombinant IL-2 were used as controls. Human cells were cultured in RPMI-1640 with 2 mM L-glutamine, 100 U/ml penicillin, 100 μg/ml streptomycin, and 10% fetal calf serum. Murine cells were grown in the same culture medium as above, but were supplemented with 10 mM non-essential amino acids, 100 mM sodium pyruvate, and 25 mM 2-mercaptoethanol (Sigma).

Three different tumor target cell lines were tested. PBMC effectors were tested against two malignant tumor target cell lines, K562 (NK sensitive) and Daudi (NK resistant). For assessment of the killing potential of T cells, activated murine splenocytes were tested against the P815 mastocytoma cell line in a tumor directed antibody-dependent cellular cytotoxicity assay (reverse ADCC)(Anderson, P. M., et al., *J. Immunol.* 142: 1383–1394 (1989)). Addition of 10 ng/ml of 145-2C11 anti-murine CD3 antibody (Boehringer Mannheim, Indianapolis, Ind.) to plates containing the Fc receptor positive P815 cell lines results in markedly augmented killing by activated T cells.

Cytotoxicity assays used 500 $^{51}$Cr-labeled tumor targets per well in V-bottom microtiter plates and effector:target ratios of 30:1, 10:1, and 3.3:1 achieved by 3-fold serial dilution of the first row prior to the addition of radiolabelled targets. Plates were centrifuged 5 min at 500 rpm to ensure cell contact, incubated 4 hr at 37° C., and then centrifuged again at 1,000 rpm. One hundred microliters of supernatant was harvested into glass scintillation vials prior to liquid scintillation counting.

None of the PEP or PEP conjugate preparations induced LAK cell killing of target cell lines in any of the cytoxicity assays described above. By comparison, recombinant human IL-2, which served as a positive control, was highly active.

Example 9

Recombinantly Engineered Vasoactive Immunoconjugate

Construction of a PEP/MAb fusion protein expression vector can be carried out using standard molecular cloning techniques. A transfer vector for a human-mouse chimeric monoclonal antibody, can be constructed and used as a parent vector. The transfer vector will carry cDNA sequences for a chimeric human-mouse heavy chain under the control of a first promoter and a chimeric human-mouse light chain under the control of a second promoter. An example of such a transfer vector is the baculovirus vector, pBVchLYM-1, of Hu et al. (*Hum. Antibod. Hybridomas* 6(1): 57–67 (1995), incorporated herein by reference.

Nucleotide sequences encoding the PEP, i.e. a cDNA subtantially homologous to SEQ ID NO: 2, will be inserted into an appropriate restriction enzyme site near the 3' end of the heavy chain gene. The resulting expression vector will encode a chimeric light chain as well as a fusion protein consisting of the chimeric heavy chain with PEP attached at the carboxy-terminus. The expression vector will be tranfected into a suitable cell line and the light chain and heavy chain fusion proteins will be co-expressed in cell cultures. The heavy and light chains of the chimeric PEP/MAb fusion protein will self assemble within the transfected cells and can be subsequently purified from the cell culture by protein A affinity chromatography.

Example 10

Clinical Use and Application

PEP immunoconjugates or fusion proteins can be used to enhance the delivery of therapeutic or tumor imaging agents. The mechanism of action of the PEP-containing molecules is to increase vascular permeability at the tumor site. In the animal model, described in Example 7, administration of PEP immunoconjugates 2.5 hours before the administration of radioiodinated MAbs produced markedly enhanced uptake of the radioactive tracer in tumors. Accordingly, the PEP immunoconjugate or fusion protein will generally be administered to the tumor host 1–3 hours before the subsequent dose of therapeutic or tumor imaging agent.

Although the present invention has been described in considerable detail with reference to certain preferred versions thereof, other versions are possible. For example, the PEP may be joined to a delivery vehicle which includes a toxin. Therefore, the spirit and scope of the appended claims should not be limited to the description of the preferred versions contained herein.

What is claimed is:

1. A method of the treatment of neoplastic tissue in a tumor bearing host, comprising:
   a) administering to a host having said tissue an effective amount of a conjugate, said conjugate comprising:
      1) a delivery vehicle having the ability to localize at the site of neoplastic tissue; and
      2) a vasoactive peptide, said peptide comprising a fragment of interleukin-2 containing amino acids 37–58; 33–58; 37–72; or 22–58 of SEQ. ID. NO. 3, wherein said peptide and said fragment are substantially free of cytokine activity, said vasoactive peptide being capable of enhancing vascular permeability when joined to a carrier, said peptide being connected to said delivery vehicle; and
   b) contemporaneously or thereafter administering to said host an antineoplastic therapeutic agent.

2. The method of claim 1, wherein said antineoplastic agent is an immunological agent.

3. The method of claim 1, wherein said antineoplastic agent is selected from the group consisting of chemotherapeutic drugs, toxins, and radionuclides.

4. A method for the treatment of neoplastic tissue in a tumor bearing host, comprising, administering to a host having said tissue an effective amount of a conjugate, said conjugate comprising:
   a) a delivery vehicle having the ability to localize at the site of neoplastic tissue;
   b) a vasoactive peptide, said peptide comprising a fragment of interleukin-2 containing amino acids 37–58; 33–58; 37–72; or 22–58 of SEQ. ID. NO. 3, wherein said peptide and said fragment are substantially free of cytokine activity, said vasoactive peptide being capable of enhancing vascular permeability when joined to a carrier, said peptide being connected to said delivery vehicle; and
   c) a tumoricidal agent.

* * * * *

UNITED STATES PATENT AND TRADEMARK OFFICE
CERTIFICATE OF CORRECTION

PATENT NO. : 6,403,096 B1  Page 1 of 1
DATED : June 11, 2002
INVENTOR(S) : Alan L. Epstein et al.

It is certified that error appears in the above-identified patent and that said Letters Patent is hereby corrected as shown below:

<u>Column 1,</u>
Line 8, before "BACKGROUND OF THE INVENTION", please insert the following paragraph:

-- STATEMENT REGARDING FEDERALLY SPONSORED RESEARCH OR DEVELOPMENT

This invention was made with government support under Contract No. NCI RO1 CA 47334 awarded by the National Institute of Health. The government has certain rights in the invention. --

Signed and Sealed this

Eighteenth Day of February, 2003

JAMES E. ROGAN
*Director of the United States Patent and Trademark Office*

UNITED STATES PATENT AND TRADEMARK OFFICE
CERTIFICATE OF CORRECTION

PATENT NO.        : 6,403,096 B1
APPLICATION NO.  : 09/443061
DATED            : June 11, 2002
INVENTOR(S)      : Epstein et al.

It is certified that error appears in the above-identified patent and that said Letters Patent is hereby corrected as shown below:

Column 19-20
SEQ ID NO:1, insert -- Thr -- between the Leu at position 15 and the Arg at position 16.
SEQ ID NO:1, insert -- Leu -- between the Glu at position 30 and the Lys at position 31.
Sequence Listing, INFORMATION FOR SEQ ID NO:3; (i) SEQUENCE CHARACTERISTICS; (A) LENGTH, delete "127" and add -- 133 --.
SEQ ID NO:3, insert -- Leu -- between the Gln at position 13 and the Glu at position 14.
SEQ ID NO:3, insert -- Thr -- between the Leu at position 35 and the Arg at position 36.
SEQ ID NO:3, insert -- Glu -- between the Glu at position 59 and the Leu at position 60.
SEQ ID NO:3, insert -- Arg -- between the Pro at position 79 and the Asp at position 80.
SEQ ID NO:3, insert -- Glu -- between the Cys at position 101 and the Tyr at position 102.

Columns 21-22
SEQ ID NO:3, insert -- Ile -- between the Ile at position 123 and the Ser at position 124.

Signed and Sealed this

Nineteenth Day of February, 2008

JON W. DUDAS
*Director of the United States Patent and Trademark Office*

SEQUENCE LISTING (1) GENERAL INFORMATION:

(iii) NUMBER OF SEQUENCES: 3

(2) INFORMATION FOR SEQ ID NO: 1:

(i) SEQUENCE CHARACTERISTICS:
            (A) LENGTH: 37 amino acids
            (B) TYPE: amino acid
            (D) TOPOLOGY: linear (ii) MOLECULE TYPE: peptide (xi) SEQUENCE DESCRIPTION: SEQ ID NO: 1:

Gln Met Ile Leu Asn Gly Ile Asn Asn Tyr L ys Asn Pro Lys Leu
                  5                   10                  15

Arg Met Leu Thr Phe Lys Phe Tyr Met Pro L ys Lys Ala Thr Glu
                 20                   25                  30

Lys His Leu Gln Cys
         35

(2) INFORMATION FOR SEQ ID NO: 2:

(i) SEQUENCE CHARACTERISTICS:
            (A) LENGTH: 111 base pairs
            (B) TYPE: nucleic acid
            (C) STRANDEDNESS: double
            (D) TOPOLOGY: linear (ii) MOLECULE TYPE: cDNA to mRNA (xi) SEQUENCE DESCRIPTION: SEQ ID NO: 2:

CAG ATG ATC CTG AAC GGT ATC AAC AAC TAC A AG AAC CCG AAA CT45
Gln Met Ile Leu Asn Gly Ile Asn Asn Tyr L ys Asn Pro Lys Leu
                  5                   10                  15

ACT CGT ATG CTG ACC TTC AAG TTC TAC ATG C CG AAG AAA GCT AC90
Thr Arg Met Leu Thr Phe Lys Phe Tyr Met P ro Lys Lys Ala Thr
                 20                   25                  30

GAA CTG AAA CAC CTG CAA TGC
Glu Leu Lys His Leu Gln Cys
             35

(2) INFORMATION FOR SEQ ID NO: 3:

(i) SEQUENCE CHARACTERISTICS:
            (A) LENGTH: 127 amino acids
            (B) TYPE: amino acid
            (D) TOPOLOGY: linear (ii) MOLECULE TYPE: peptide (xi) SEQUENCE DESCRIPTION: SEQ ID NO: 3:

Ala Pro Thr Ser Ser Ser Thr Lys Lys Thr G ln Leu Gln Glu His
                  5                   10                  15

Leu Leu Leu Asp Leu Gln Met Ile Leu Asn G ly Ile Asn Asn Tyr
                 20                   25                  30

Lys Asn Pro Lys Leu Arg Met Leu Thr Phe L ys Phe Tyr Met Pro
                 35                   40                  45

Lys Lys Ala Thr Glu Leu Lys His Leu Gln C ys Leu Glu Glu Leu
                 50                   55                  60

Lys Pro Leu Glu Glu Val Leu Asn Leu Ala G ln Ser Lys Asn Phe
                 65                   70                  75

His Leu Arg Pro Asp Leu Ile Ser Asn Ile A sn Val Ile Val Leu
                 80                   85                  90

Glu Leu Lys Gly Ser Glu Thr Thr Phe Met C ys Tyr Ala Asp Glu
                 95                  100                 105

```
Thr Ala Thr Ile Val Glu Phe Leu Asn Arg Trp Ile Thr Phe Cys
            110                 115                 120

Gln Ser Ile Ser Thr Leu Thr
                125
```